United States Patent
Merianos

(10) Patent No.: US 7,087,762 B2
(45) Date of Patent: Aug. 8, 2006

(54) LONG-LASTING ANTIMICROBIAL REACTION PRODUCT OF ALLANTOIN AND FORMALDEHYDE CONTAINING A LOW LEVEL OF FREE FORMALDEHYDE

(75) Inventor: John J. Merianos, Middletown, NJ (US)

(73) Assignee: ISP Investments Inc., Wilmington, DE (US)

( * ) Notice: Subject to any disclaimer, the term of this patent is extended or adjusted under 35 U.S.C. 154(b) by 0 days.

(21) Appl. No.: 11/121,547

(22) Filed: May 4, 2005

(65) Prior Publication Data

US 2005/0203157 A1   Sep. 15, 2005

Related U.S. Application Data

(63) Continuation-in-part of application No. 10/302,093, filed on Nov. 22, 2002, now abandoned.

(51) Int. Cl.
*C07D 233/78* (2006.01)

(52) U.S. Cl. .................................. 548/318.1

(58) Field of Classification Search ............. 548/318.1, 548/317.1, 318.5; 514/390
See application file for complete search history.

(56) References Cited

U.S. PATENT DOCUMENTS 3,248,285 A * 4/1966 Berke .......................... 514/390

* cited by examiner

*Primary Examiner*—Kamal A. Saeed
*Assistant Examiner*—Michael P. Barker
(74) *Attorney, Agent, or Firm*—William J. Davis; Walter Katz

(57) ABSTRACT

This invention relates to a reaction product of allantoin and formaldehyde made in a molar ratio of about 1:2.75–1:3.25, preferably 1:3, respectively, preferably under controlled pH (5.0 to 7.0) and temperature (40° to 85° C., preferably 50–60° C.) conditions, which product contains free formaldehyde (<0.1%), and methylene diol of about 580–1385 ppm, preferably at a pH of 7.2, with advantageous long-lasting, anti-microbial properties, particularly against the organism *B. cepacia*, and in combination products with parabens and iodopropynyl butyl carbamate (IPBC).

5 Claims, No Drawings

LONG-LASTING ANTIMICROBIAL REACTION PRODUCT OF ALLANTOIN AND FORMALDEHYDE CONTAINING A LOW LEVEL OF FREE FORMALDEHYDE

CROSS REFERENCE TO RELATED APPLICATION

The present application is a continuation-in-part of application Ser. No. 10/302,093, filed Nov. 22, 2002, now abandoned.

BACKGROUND OF THE INVENTION

1. Field of the Invention

This invention relates to reaction products of allantoin and formaldehyde and, more particularly, to such products which contain very low levels of free formaldehyde (<0.1%), while retaining advantageous, long-lasting anti-microbial properties, particularly against the organism B. cepacia.

2. Description of the Prior Art

Berke, P. A., in U.S. Pat. No. 3,248,285 described a reaction product of allantoin and formaldehyde (Germall® 115) from the reactants in a mole ratio of 1:1.5, respectively; and in U.S. Pat. No. 4,271,176 and Reissue 32,848, (Germall® II) in a mole ratio of 1:4. However, during recent evaluations using modern $C^{13}$ NMR techniques, these reaction products were found to contain 0.5% to 1.0% of free formaldehyde. This amount was considered in the past to be necessary to retain its anti-microbial activity; although now it is recognized that a considerable amount of free formaldehyde in the product is disadvantageous from a safety (irritation) and environmental standpoints.

Accordingly, it is an object of this invention to prepare reaction products of allantoin and formaldehyde which have long-lasting anti-microbial properties with the presence therein of only very low levels of free formaldehyde (i.e. <0.1%).

Another object of the invention is to provide a method of making such effective reaction products.

Still another object of this invention is to provide a synergistic combination of such products with other known fungicides to obtain broad spectrum activity against bacteria and fungi, yeast, molds, and the like.

SUMMARY OF THE INVENTION

This invention relates to a reaction product of allantoin and formaldehyde,

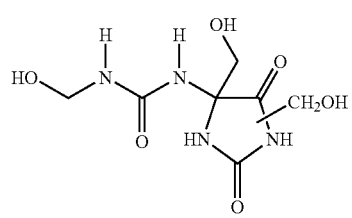

which is

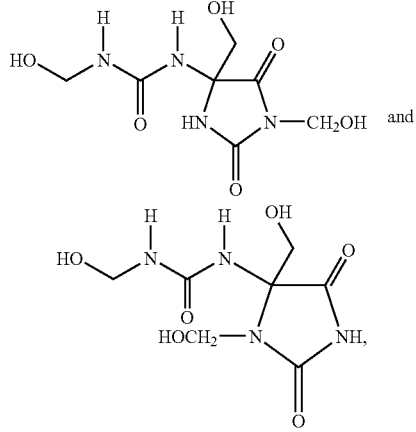

or mixtures thereof, made in a molar ratio of about 1:2.75–1:3.25, preferably 1:3, respectively, preferably under controlled pH (5.0 to 7.0) and temperature (40° to 60° C.) conditions, which contains substantially no free formaldehyde (<0.1%), with advantageous long-lasting, broad spectrum anti-microbial properties, particularly against the organism B. cepacia.

What has been discovered herein is that reaction products of allantoin and formaldehyde result in free formaldehyde being present in equilibrium with methylene diol and N-methylol. Unexpectedly, it was discovered that N-methylol and methylene diol, work in synergy to act as long-lasting anti-microbial agents, i.e. both can slowly react to provide anti-microbial protection against a wide range of microbes, including the difficult to kill B. cepacia, while free formaldehyde is present in very low concentrations (<0.1%) in equilibrium with methylene diol.

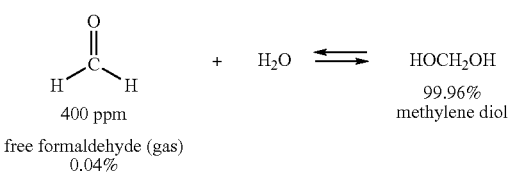

Both equilibrium moieties can react with the amide moieties of allantoin to form several N-methylol of the allantoin compounds, which are stabilized by H-bonding; however they can slow hydrolyzed in water to give the methylene diol intermediate, which can react with amide to form N-methylols.

DETAILED DESCRIPTION OF THE INVENTION

The following examples describe preparation of Comparative Reaction Products (CRP) for (A) Germall® 115 (1:1.5); at low caustic levels; and (B) at high caustic levels; and (C) Germall® II (1:4), low caustic and (D) high caustic; and Invention Reaction Products (IRP) Germall® III (1:3), (A) laboratory and (B) commercial runs, with only enough caustic to neutralize the formic acid present in the Formalin solution.

Comparative Reaction Products

| A. GERMALL ® 115 (1:1.5) | |
| --- | --- |
| Allantoin | 15.8 g (0.1 mole) |
| Formalin (37%) | 12.2 g (0.15 mole) |
| Water | 28.5 ml |

The above mixture was refluxed for one hour to form a clear solution.

| B. GERMALL ® 115 (High Caustic) (1:1.5) | |
| --- | --- |
| Allantoin | 600 g (3.8 mole) |
| Formalin (37%) | 450 g (5.5 mole) |
| Sodium Hydroxide | 123 g |

Refluxed for one hour to form a clear solution. Concentrated acetic acid was added to adjust the Ph to 4.0. Removed water to give a white powder.

| C. GERMALL ® II (1:4) | |
| --- | --- |
| Allantoin | 1053 g (6.66 mole) |
| Formalin (37%) | 2160 g (26.64 mole) |

The white suspension was heated to 85° C. and held for an additional hour; upon cooling a clear solution was obtained. Removed water under reduced pressure to give a white powder.

| D. GERMALL ® II (1:4) | |
| --- | --- |
| Allantoin | 158.1 g (1.0 mole) |
| Formalin (37%) | 324.2 g (3.99 mole) |
| Sodium Hydroxide 10% | 32.0 g (0.08 mole) |

Refluxed at 85° C. for one hour. The clear colorless solution obtained was dried under reduced pressure to give solid white powder residue.

Comparative Test Results

Activity against yeast and mold:
0.3% test solutions.

| TEST SOLUTIONS | C. Albican ATTC1023 | A. Niger ATCC 9642(for 3 Days) |
| --- | --- | --- |
| 0.3% Germall ® 115 (Exs. A/B) | + | + |
| 0.3% Germall ® II(Exs. C/D) | − | − |

+ Growth
− No Growth

Invention Reaction Product

| A. (LABORATORY SCALE) (GERMALL ® III) (1:3) | |
| --- | --- |
| Allantoin | 1616 g (10.23 mole) |
| Formalin LM*(37%) | 2488 g (30.68 mole) |
| Sodium Hydroxide 50% | 24 g |

*LM = low methanol (<0.5%) Borden Chemicals

Mixed and heated at 60° C. for 3 hours to give a clear solution. The Ph of the product was adjusted to 7.2 with the sodium hydroxide solution to neutralize formic acid in Formalin® and the solution was spray dried to give a free-flowing, white powder.

Invention Reaction Product

| B. (COMMERCIAL SCALE) (GERMALL ® III) (1:3) | |
| --- | --- |
| Allantoin.wet cake | 2095 lbs (10.23 mole) |
| Formalin LM (37%) | 2488 lbs (30.68 mole) |
| Sodium Hydroxide 50% | 23.6 lbs |
| Ph | 6.5–7.0 |
| Reaction Temp | 40–60° C. |

The resultant mixture then was further reacted at 85° C. for 3 hours to give a clear solution at pH 7.2. The solution was spray dried to remove water and other volatile by-products to give a free-flowing, white powder.

A study was conducted to determine the level of methylene diol in the reaction products versus the number of equivalents of formaldehyde added during formation. These results are based on quantitative 13C-NMR analysis and summarized in Table 1 below.

TABLE 1

| Number of Equivalents Formaldehyde/Allantoin | ppm Methylene Diol |
| --- | --- |
| 4.00 | 3545 |
| 3.50 | 1916 |
| 3.25 | 1385 |
| 3.00 | 790 |
| 2.75 | 583 |
| 2.50 | 340 |
| 1.50 | 250 |

TABLE 2

BIOACTIVITY OF GERMALL ® COMPOUNDS

| INVENTION EXS. PRESERVATIVE | ORGANISM | STATIC | CIDAL |
| --- | --- | --- | --- |
| IRP - Germall ® III (1:3) | Staph aureus | 300 ppm | 1250 ppm |
| | E. coli | 300 ppm | 1250 ppm |
| | P. aeruginosa | 300 ppm | 600 ppm |
| | B. cepacia | 150 ppm | 300 ppm |
| | C. albicans | >5000 ppm | — |
| | A. niger | 2500 ppm | 2500 ppm |
| CRP - Germall ® II (1:4) | Staph aureus | 300 ppm | 1250 ppm |
| | E. coli | 600 ppm | 1250 ppm |
| | P. aeruginosa | 600 ppm | 1250 ppm |

TABLE 2-continued

BIOACTIVITY OF GERMALL ® COMPOUNDS

| INVENTION EXS. PRESERVATIVE | ORGANISM | STATIC | CIDAL |
|---|---|---|---|
| | B. cepacia | 150 ppm | 600 ppm |
| | C. albicans | 5000 ppm | >5000 ppm |
| | A. niger | 2500 ppm | 2500 ppm |
| CRP - Germall ® 115 (1:1.5) | Staph aureus | 1250 ppm | 2500 ppm |
| | E. coli | 1250 ppm | 2500 ppm |
| | P. aeruginosa | 1250 ppm | 2500 ppm |
| | B. cepacia | 600 ppm | 1250 ppm |
| | C. albicans | >5000 ppm | |
| | A. niger | 5000 ppm | 5000 ppm |

Protocol

Minimum Inhibitory Concentration (MIC) Test Method

Scope

The purpose of this test procedure is to screen experimental compounds for anti-microbial activity.

Principle

The measurement of the lowest effective concentration of an anti-microbial or anti-microbial blend is important for recommending use concentrations. The MIC test is an in vitro tube dilution procedure used to identify effective concentrations of anti-microbials. In this test, the experimental compound is diluted by serial concentrations into nutrient culture media. Test organisms are then inoculated into the anti-microbial solutions.

If the experimental compound is effective, there is no growth observed in the test dilution tubes and they are clear. If the experimental compound is not effective, the test dilution tubes are cloudy, indicating growth. This test will determine static as well as cidal activity concentrations.

Materials

1. Laminar flow hood (Baker Sterilgard SG 400)
2. 18×150 mm culture tubes
3. Stock antimicrobial solution
4. Media: Trypticase soy broth (BBL 11043) and AOAC Letheen broth (BBL 10914)
5. Test organisms: *Staphylococcus aureus* ATCC 6538, *Escherichia coli* ATCC 8739, *Pseudomonas aeruginosa* ATCC 9027, *Burkholderia cepacia* ATCC 25416, *Candida albicans* ATCC 10231, and *Aspergillus niger* ATCC 16404.
6. Spectrophotometer (Spectronic 20D, Milton Roy)

Minimum Inhibitory Concentration Test

Procedure

1. Antimicrobial stock solutions are prepared at predetermined concentrations (i.e., 10% through 0.07%) depending on the test material. Serial doubling dilutions are made as follows. Each culture tube contains 5 mls of trypticase soy broth. Five mls of the stock solution are added to the first tube and vortexed. 5 mls are then removed and placed into the second tube, (and so on, until the last tube). At the final test concentration, 5 mls of the broth/antimicrobial mixture is decanted out.
2. The test organisms are prepared as with any organism inoculum (MLM 100-3, MLM 100-4, and MLM 100-5).

A saline suspension of each organism is prepared. The bacterial organisms and the yeast are a standardized at a concentration of $1 \times 10^6$ cfu/ml. The mold inoculum is approximately $1 \times 10^5$ cfu/ml.

3. Inoculate each culture tube with 0.10 mls of organism inoculum and vortex.
4. Incubate bacterial tubes for 24 hours at 35° C. Incubate yeast or mold tubes for 48 hours at 25° C. Read for growth; turbid tubes for bacteria and yeast; mold clearly visible tubes. This is the minimum inhibitory concentration (static activity).
5. After the tubes are read, transfer all "clear" tubes and the first cloudy (growth) tube into Letheen broth containing neutralizers. Incubate the Letheen broth tubes for 48 hours at the bacterial or fungal incubation temperatures. Read for growth; turbid tubes for bacteria and yeast; mold clearly visible in mold tubes. This is the cidal activity concentration.

Discussion

The cidal activity of an anti-microbial can be rapidly screened by means of a MIC test before further evaluation tests, such as longer preservative efficacy tests, are performed. This test is a tube serial dilution procedure limited only by the water solubility of the material. Where anti-microbial materials are slightly insoluble, leaving the TSB broth turbid, a procedure modification can be made. Tubes are incubated for 24 hours (bacteria) or 48 hours (fungi) but instead of transfer to Letheen broth, the TSB tubes are streaked onto Letheen agar. The agar plates are then incubated appropriately and then read for absence or presence of growth. Depending on the degree of insolubility, a measure of cidal activity may be the only parameter measured.

Anti-microbial neutralization is important in this screening test. Letheen broth or agar contains neutralizers but if these do not neutralize the anti-microbial adequately, others can be added. These are to be determined prior to testing.

Aseptic technique is important in any microbiological procedure. All functional operations are performed under the laminar flow hood with use of sterile pipettes, tubes and media to eliminate cross-contamination. Surface sanitizers (i.e., alcohol) are used on the work surface before and after each operation. Ample time is allowed for recirculation of air within the sterile chamber of the hood.

The bioactivity data show particular effectiveness against the organism cepacia B. (cidal=300 ppm vs. 600 ppm and 1250 ppm for Germall® II and Germall® 115, respectively). However, if desired, even broader spectrum antibacterial activity can be achieved by combination products with the invention composition whose formulations are given below.

Invention Combination Products

| | COMBINATION BLENDS (BY WEIGHT) | |
|---|---|---|
| (1) | Germall ® III | 20–30% |
| | MP - methyl paraben | 8–12% |
| | PP - propyl paraben | 2–4% |
| | PG - propylene glycol | q.s. 100 |
| (2) | Germall ® III | 40–45% |
| | IPBC - iodopropynyl butyl carbamate | 0.5–5% |
| | PG - propylene glycol | qs 100 |
| (3) | Germall ® III | 98.5–99.5% |
| | IPBC - iodopropynyl butyl carbamate (Powder) | 0.5–1.5% |

Preservative Activity (Challenge Test)

A typical cosmetic emulsion was prepared for microbiological challenge testing and predetermined admixtures of a methylol compound and IPBC were added at various use levels. The emulsion thus prepared had the following composition:

NONIONIC EMULSION (UNPRESERVED CONTROL)

| Phase | Ingredient | % wt. |
|---|---|---|
| A | Water | 69.80 |
| A | Carbomer | 10.00 |
| B | Octyl Palmitate | 5.00 |
| B | Cetearyl alcohol and Ceteareth-20 | 2.00 |
| B | Glyceryl Stearate and Laureth-23 | 2.50 |
| B | Mineral Oil | 5.00 |
| C | Triethanolamine (99%) | 0.20 |
| D | Preservative | 0.00 |
| E | Hydrolyzed Collagen | 0.50 |
| E | Water | 5.00 |
|  | Total | 100.00 |

Procedure:
Heat Phase A to 75° C. Heat Phase B to 75° C.
Add Phase B to Phase A. Mix until uniform.
Add Phase C. Remove heat.
Add Phase D at the appropriate temperature.
Add Phase E at 40° C.
Continue mixing to 30° C.

STANDARD SCREENING EMULSIONS

|  | % wt. |
|---|---|
| Phase A | |
| Stearic Acid | 5.00 |
| Mineral Oil | 2.50 |
| Cetyl Alcohol | 1.00 |
| Lareth-5 and Ceteth-5 and Oleth-5 and Steareth-5 | 0.50 |
| Glycerol Monostearate and Polyoxyethylene Stearate | 1.50 |
| Phase B | |
| Deionized Water | 88.0 |
| Triethanolamine 99% | 1.00 |
| Citric Acid 30% aqueous solution | 0.60 |
| Preservative Admixture | qs |

To prepare the emulsion, Phases A and B were heated separately to 75°–80° C. Phase A then was added to Phase B with mixing. The mixture then was cooled to 55°–60° C. At this point the desired amount of the preservative admixture was added and the product was cooled to 50° C. while stirring. The citric acid solution then was added to adjust the pH and the mixture was stirred until a temperature of 30° C. was reached.

The challenge tests were carried out using the following microorganisms: SA, ECOLI, PSA, PC, AN and CAN, in this manner. 50 g aliquots of the test emulsion containing various amounts of the preservative admixture were inoculated with approximately $10^7$–$10^8$ of the challenge organisms. The test samples then were stirred to disperse the challenge inoculum. The samples were incubated and assayed at 48 hours, 7, 14, 21 and 28 days. The assays were performed on 1 g of the test sample by serially diluting $10^1$ to $10^6$ of the original concentration. The plating medium for bacteria was Letheen agar and for fungi it was low pH Mycophil agar with Tween 20. Each plated sample was incubated for 48 hours at 37° C. for bacteria, 5 days at 25° C. for mold, and 3 days at 25° C. for fungi. After incubation, readings of the number of colonies per milliliter (cfu/ml) were made. At 21 days the test product was reinoculated with half of the original inoculum. The data is presented in Tables 3–11 below.

Challenge Tests

TABLE 3

COMPARISON OF ACTIVITY OF GERMALL III TO GERMALL II AND 115 (SCREENING EMULSION)

| Preservative | Conc. | Organism | 48 hrs | 7 days | 14 days | 21 days | 28 days |
|---|---|---|---|---|---|---|---|
| Germall II | 1000 ppm | SA | <10 | <10 | <10 | <10 | <10 |
| | | EC | <10 | <10 | <10 | <10 | <10 |
| | | PSA | <10 | <10 | <10 | <10 | <10 |
| | | BC | <10 | <10 | <10 | <10 | <10 |
| | | CAN | 160,000 | 78,000 | 63,000 | 260,000 | 210,000 |
| | | AN | <10 | <10 | <10 | <10 | <10 |
| Germall III | 1000 ppm | SA | <10 | <10 | <10 | <10 | <10 |
| | | EC | <10 | <10 | <10 | <10 | <10 |
| | | PSA | <10 | <10 | <10 | <10 | <10 |
| | | BC | <10 | <10 | <10 | <10 | <10 |
| | | CAN | 160,000 | 380,000 | 380,000 | 810,000 | 640,000 |
| | | AN | <10 | <10 | <10 | <10 | <10 |
| Germall 115 | 2000 ppm | SA | 3000 | <10 | <10 | <10 | <10 |
| | | EC | 490 | <10 | <10 | <10 | <10 |
| | | PSA | <10 | <10 | <10 | <10 | <10 |
| | | BC | <10 | <10 | <10 | <10 | <10 |
| | | CAN | 230,000 | 2,000,000 | 650,000 | 1,500,000 | 1,200,000 |
| | | AN | <10 | <10 | <10 | <10 | <10 |

TABLE 3-continued

COMPARISON OF ACTIVITY OF GERMALL III TO GERMALL II AND 115
(SCREENING EMULSION)

| Preservative | Conc. | Organism | 48 hrs | 7 days | 14 days | 21 days | 28 days |
|---|---|---|---|---|---|---|---|
| Germall II | 2000 ppm | SA | <10 | <10 | <10 | <10 | <10 |
| | | EC | <10 | <10 | <10 | <10 | <10 |
| | | PSA | <10 | <10 | <10 | <10 | <10 |
| | | BC | <10 | <10 | <10 | <10 | <10 |
| | | CAN | 150 | 9,600 | 48,900 | 490,000 | 210,000 |
| | | AN | <10 | <10 | <10 | <10 | <10 |
| Germall III | 2000 ppm | SA | <10 | <10 | <10 | <10 | <10 |
| | | EC | <10 | <10 | <10 | <10 | <10 |
| | | PSA | <10 | <10 | <10 | <10 | <10 |
| | | BC | <10 | <10 | <10 | <10 | <10 |
| | | CAN | 6000 | 195,000 | 460,000 | 690,000 | 1,070,000 |
| | | AN | <10 | <10 | <10 | <10 | <10 |
| Unpreserved | 0 | SA | 2,100,000 | 57,000 | 90 | <10 | 68,000 |
| | | EC | 37,000 | 96,000 | 96,000 | 43,000 | 790,000 |
| | | PSA | 70 | 4600 | 500 | 10,100 | 170,000 |
| | | BC | 2,100,000 | 860,000 | 1,520,000 | 3,520,000 | >10 E6 |
| | | CAN | 1,100,000 | 168,000 | 67,000 | 270,000 | 460,000 |
| | | AN | 700,000 | 56,000 | 44,000 | 190,000 | 320,000 |

TABLE 4

COMPARISON OF ACTIVITY OF GERMALL III TO GERMALL II AND 115
(NONIONIC EMULSION)

| Preservative | Conc. | Organism | 48 hrs | 7 days | 14 days | 21 days | 28 days |
|---|---|---|---|---|---|---|---|
| Germall III | 2000 ppm | SA | <10 | <10 | <10 | <10 | <10 |
| | | EC | <10 | <10 | <10 | <10 | <10 |
| | | PSA | <10 | <10 | <10 | <10 | <10 |
| | | BC | <10 | <10 | <10 | <10 | <10 |
| | | CAN | 820,000 | 1,680,000 | 1,350,000 | 700,000 | >1E6 |
| | | AN | <10 | <10 | <10 | <10 | <10 |
| Germall II | 2000 ppm | SA | <10 | <10 | <10 | <10 | <10 |
| | | EC | <10 | <10 | <10 | <10 | <10 |
| | | PSA | <10 | <10 | <10 | <10 | <10 |
| | | BC | <10 | <10 | <10 | <10 | <10 |
| | | CAN | 320,000 | 720,000 | 650,000 | 730,000 | >1E6 |
| | | AN | <10 | <10 | <10 | <10 | <10 |
| Germall 115 | 2000 ppm | SA | 1,500 | <10 | <10 | <10 | <10 |
| | | EC | 52,000 | <10 | <10 | <10 | <10 |
| | | PSA | <10 | <10 | <10 | <10 | <10 |
| | | BC | <10 | <10 | <10 | <10 | <10 |
| | | CAN | >1E6 | >1E6 | >1E6 | 700,000 | >1E6 |
| | | AN | <10 | 20 | 390 | 370 | >1E4 |
| Germall III | 4000 ppm | SA | <10 | <10 | <10 | <10 | <10 |
| | | EC | <10 | <10 | <10 | <10 | <10 |
| | | PSA | <10 | <10 | <10 | <10 | <10 |
| | | BC | <10 | <10 | <10 | <10 | <10 |
| | | CAN | 24,000 | >1E6 | >1E6 | 730,000 | >1E6 |
| | | AN | <10 | <10 | <10 | <10 | <10 |
| Germall II | 4000 ppm | SA | <10 | <10 | <10 | <10 | <10 |
| | | EC | <10 | <10 | <10 | <10 | <10 |
| | | PSA | <10 | <10 | <10 | <10 | <10 |
| | | BC | <10 | <10 | <10 | <10 | <10 |
| | | CAN | 50 | 10,000 | 620,000 | 460,000 | >1E6 |
| | | AN | <10 | <10 | <10 | <10 | <10 |
| Germall 115 | 4000 ppm | SA | <10 | <10 | <10 | <10 | <10 |
| | | EC | 1,500 | <10 | <10 | <10 | <10 |
| | | PSA | <10 | <10 | <10 | <10 | <10 |
| | | BC | <10 | <10 | <10 | <10 | <10 |
| | | CAN | 1,060,000 | 1,000,000 | >1E6 | >1E6 | >1E6 |
| | | AN | <10 | <10 | <10 | <10 | <10 |
| Unpreserved | 0 | SA | >1E6 | 6,300 | >1E4 | <10 | >1E4 |
| | | EC | >1E6 | 900,000 | >1E4 | >1E4 | >1E4 |
| | | PSA | 20,000 | >1E6 | >1E4 | >1E4 | >1E4 |
| | | BC | >1E6 | >1E6 | >1E4 | >1E4 | >1E4 |
| | | CAN | >1E6 | >1E6 | >1E4 | >1E4 | >1E4 |
| | | AN | 500,000 | 510,000 | >1E4 | >1E4 | >1E4 |

TABLE 5

COMPARISON OF ACTIVITY OF GERMALL III TO GERMALL II AND 115
(SCREENING EMULSION)

| Preservative | Conc. | Organism | 48 hrs | 7 days | 14 days | 21 days | 28 days |
|---|---|---|---|---|---|---|---|
| Germall III | 250 ppm | SA | 69,000 | <10 | <10 | <10 | <10 |
| | | EC | 11,000 | <10 | <10 | <10 | <10 |
| | | PSA | <10 | <10 | <10 | <10 | <10 |
| | | BC | 200 | <10 | <10 | <10 | <10 |
| | | CAN | 430,000 | 120,000 | 70,000 | 150,000 | 850,000 |
| | | AN | 100,000 | 200 | 70 | 40 | 1,300 |
| Germall II | 250 ppm | SA | 55,000 | <10 | <10 | <10 | <10 |
| | | EC | 5500 | <10 | <10 | <10 | <10 |
| | | PSA | <10 | <10 | <10 | <10 | <10 |
| | | BC | <10 | <10 | <10 | <10 | <10 |
| | | CAN | 290,000 | 170,000 | 71,000 | 46,000 | 680,000 |
| | | AN | 50,000 | <10 | <10 | <10 | 100 |
| Germall 115 | 250 ppm | SA | 117,000 | 30 | <10 | <10 | 1,500 |
| | | EC | 40,000 | 20 | <10 | <10 | 3600 |
| | | PSA | <10 | 320 | >1E4 | >1E6 | >1E6 |
| | | BC | 11,000 | >1E6 | >1E6 | >1E6 | >1E6 |
| | | CAN | 1,090,000 | 270,000 | 1,120,000 | 770,000 | >1E6 |
| | | AN | 90,000 | 20,000 | 20,000 | 29,000 | 300,000 |
| Germall III | 500 ppm | SA | 38,000 | <10 | <10 | <10 | <10 |
| | | EC | 18,000 | <10 | <10 | <10 | <10 |
| | | PSA | <10 | <10 | <10 | <10 | <10 |
| | | BC | <10 | <10 | <10 | <10 | <10 |
| | | CAN | 100,000 | 210,000 | 310,000 | 270,000 | >1E6 |
| | | AN | 9000 | <10 | <10 | <10 | <10 |
| Germall II | 500 ppm | SA | 17,000 | <10 | <10 | <10 | <10 |
| | | EC | 610 | <10 | <10 | <10 | <10 |
| | | PSA | <10 | <10 | <10 | <10 | <10 |
| | | BC | <10 | <10 | <10 | <10 | <10 |
| | | CAN | 170,000 | 100,000 | 90,000 | 320,000 | 930,000 |
| | | AN | 40 | <10 | <10 | <10 | <10 |
| Germall 115 | 500 ppm | SA | 140,000 | <10 | <10 | <10 | <10 |
| | | EC | 24,000 | <10 | <10 | <10 | <10 |
| | | PSA | <10 | <10 | <10 | <10 | <10 |
| | | BC | <10 | <10 | <10 | <10 | <10 |
| | | CAN | 290,000 | 760,000 | 790,000 | 1,210,000 | >1E6 |
| | | AN | 130,000 | 1,000 | 40 | 290 | 80,000 |
| Unpreserved | 0 | SA | >1E6 | 34,000 | 6,800 | 20 | >1E4 |
| | | EC | 18,000 | 4,900 | >1E4 | >1E4 | >1E4 |
| | | PSA | 50 | >1E4 | >1E4 | >1E4 | >1E4 |
| | | BC | >1E6 | >1E6 | >1E4 | >1E4 | >1E4 |
| | | CAN | 970,000 | 270,000 | >1E4 | >1E4 | >1E4 |
| | | AN | 150,000 | 280,000 | >1E4 | >1E4 | >1E4 |

TABLE 6

COMPARISON OF ACTIVITY OF GERMALL PLUS AND GERMALL III/IPBC
(SCREENING EMULSION)

| Preservative | Conc. | Organism | 48 hrs | 7 days | 14 days | 21 days | 28 days |
|---|---|---|---|---|---|---|---|
| Germall Plus | | SA | <10 | <10 | <10 | <10 | <10 |
| Germall II | 1980 | EC | <10 | <10 | <10 | <10 | <10 |
| IPBC | 20 | PSA | <10 | <10 | <10 | <10 | <10 |
| | | BC | <10 | <10 | <10 | <10 | <10 |
| | | CAN | <10 | <10 | <10 | <10 | <10 |
| | | AN | <10 | <10 | <10 | <10 | <10 |
| Germall III | 1980 | SA | <10 | <10 | <10 | <10 | <10 |
| IPBC | 20 | EC | <10 | <10 | <10 | <10 | <10 |
| | | PSA | <10 | <10 | <10 | <10 | <10 |
| | | BC | <10 | <10 | <10 | <10 | <10 |
| | | CAN | <10 | <10 | <10 | <10 | <10 |
| | | AN | <10 | <10 | <10 | <10 | 100 |
| Germall III | 1960 | SA | <10 | <10 | <10 | <10 | <10 |
| IPBC | 40 | EC | <10 | <10 | <10 | <10 | <10 |
| | | PSA | <10 | <10 | <10 | <10 | <10 |
| | | BC | <10 | <10 | <10 | <10 | <10 |
| | | CAN | <10 | <10 | <10 | <10 | <10 |
| | | AN | <10 | <10 | <10 | <10 | <10 |
| Unpreserved | | SA | 580,000 | 3200 | 180 | <10 | >1E4 |
| | | EC | 5,200 | 70,000 | >1E4 | >1E4 | >1E4 |
| | | PSA | 18,000 | 40,000 | >1E4 | >1E4 | >1E4 |

TABLE 6-continued

COMPARISON OF ACTIVITY OF GERMALL PLUS AND GERMALL III/IPBC (SCREENING EMULSION)

| Preservative | Conc. | Organism | 48 hrs | 7 days | 14 days | 21 days | 28 days |
|---|---|---|---|---|---|---|---|
| | | BC | >1E6 | >1E6 | >1E4 | >1E4 | >1E4 |
| | | CAN | >1E6 | 200,000 | >1E4 | >1E4 | >1E4 |
| | | AN | 210,000 | 270,000 | >1E4 | >1E4 | >1E4 |

TABLE 7

COMPARISON OF ACTIVITY OF LIQUID GERMALL PLUS AND GERMALL III/IPBC-LIQ (SCREENING EMULSION)

| Preservative | Conc. | Organism | 48 hrs | 7 days | 14 days | 21 days | 28 days |
|---|---|---|---|---|---|---|---|
| LiqGermPlus | | SA | <10 | <10 | <10 | <10 | <10 |
| Germall II | 790 | EC | <10 | <10 | <10 | <10 | <10 |
| IPBC | 10 | PSA | <10 | <10 | <10 | <10 | <10 |
| | | BC | <10 | <10 | <10 | <10 | <10 |
| | | CAN | 8,000 | <10 | <10 | <10 | <10 |
| | | AN | <10 | <10 | <10 | <10 | <10 |
| LiqGermPlus | | SA | <10 | <10 | <10 | <10 | <10 |
| Germall II | 1580 | EC | <10 | <10 | <10 | <10 | <10 |
| IPBC | 20 | PSA | <10 | <10 | <10 | <10 | <10 |
| | | BC | <10 | <10 | <10 | <10 | <10 |
| | | CAN | <10 | <10 | <10 | <10 | <10 |
| | | AN | <10 | <10 | <10 | <10 | 100 |
| Germall III | 790 | SA | <10 | <10 | <10 | <10 | <10 |
| IPBC | 10 | EC | <10 | <10 | <10 | <10 | <10 |
| Liquid | | PSA | <10 | <10 | <10 | <10 | <10 |
| | | BC | <10 | <10 | <10 | <10 | <10 |
| | | CAN | 26,000 | <10 | <10 | <10 | <10 |
| | | AN | <10 | <10 | <10 | <10 | <10 |
| Germall III | 1580 | SA | <10 | <10 | <10 | <10 | <10 |
| IPBC | 20 | EC | <10 | <10 | <10 | <10 | <10 |
| Liquid | | PSA | <10 | <10 | <10 | <10 | <10 |
| | | BC | <10 | <10 | <10 | <10 | <10 |
| | | CAN | <10 | <10 | <10 | <10 | <10 |
| | | AN | <10 | <10 | <10 | <10 | <10 |
| Unpreserved | 0 | SA | 580,000 | 3200 | 180 | <10 | >1E4 |
| | | EC | 5200 | 70,000 | >1E4 | >1E4 | >1E4 |
| | | PSA | 18,000 | 40,000 | >1E4 | >1E4 | >1E4 |
| | | BC | >1E6 | >1E6 | >1E4 | >1E4 | >1E4 |
| | | CAN | >1E6 | 200,000 | >1E4 | >1E4 | >1E4 |
| | | AN | 210,000 | 270,000 | >1E4 | >1E4 | >1E4 |

TABLE 8

COMPARISON OF ACTIVITY OF GERMALL PLUS AND GERMALL III/IPBC (SCREENING EMULSION)

| Preservative | Conc. | Organism | 48 hrs | 7 days | 14 days | 21 days | 28 days |
|---|---|---|---|---|---|---|---|
| Germall Plus | | SA | 42,000 | <10 | <10 | <10 | <10 |
| Germall II | 495 | EC | 40 | <10 | <10 | <10 | <10 |
| IPBC | 5 | PSA | <10 | <10 | <10 | <10 | <10 |
| | | BC | <10 | <10 | <10 | <10 | <10 |
| | | CAN | 48,000 | <10 | <10 | <10 | <10 |
| | | AN | 100 | <10 | <10 | <10 | <10 |
| Germall Plus | | SA | 300 | <10 | <10 | <10 | <10 |
| Germall II | 990 | EC | <10 | <10 | <10 | <10 | <10 |
| IPBC | 10 | PSA | <10 | <10 | <10 | <10 | <10 |
| | | BC | <10 | <10 | <10 | <10 | <10 |
| | | CAN | <10 | <10 | <10 | <10 | <10 |
| | | AN | <10 | <10 | <10 | <10 | <10 |
| Germall III | 495 | SA | 46,000 | <10 | <10 | <10 | <10 |
| IPBC | 5 | EC | 25,000 | <10 | <10 | <10 | <10 |
| | | PSA | <10 | <10 | <10 | <10 | <10 |
| | | BC | <10 | <10 | <10 | <10 | <10 |
| | | CAN | 11,000 | <10 | <10 | <10 | <10 |
| | | AN | <10 | <10 | <10 | <10 | <10 |

TABLE 8-continued

COMPARISON OF ACTIVITY OF GERMALL PLUS AND GERMALL III/IPBC
(SCREENING EMULSION)

| Preservative | Conc. | Organism | 48 hrs | 7 days | 14 days | 21 days | 28 days |
|---|---|---|---|---|---|---|---|
| Germall III | 990 | SA | 24,000 | <10 | <10 | <10 | <10 |
| IPBC | 10 | EC | 1,000 | <10 | <10 | <10 | <10 |
| | | PSA | 19,000 | <10 | <10 | <10 | <10 |
| | | BC | >1E6 | <10 | <10 | <10 | <10 |
| | | CAN | 2,500 | <10 | <10 | <10 | <10 |
| | | AN | <10 | <10 | <10 | <10 | <10 |
| Germall III | 490 | SA | 23,000 | <10 | <10 | <10 | <10 |
| IPBC | 10 | EC | 900 | <10 | <10 | <10 | <10 |
| | | PSA | 18,000 | <10 | <10 | <10 | <10 |
| | | BC | >1E6 | <10 | <10 | <10 | <10 |
| | | CAN | 2800 | <10 | <10 | <10 | <10 |
| | | AN | <10 | <10 | <10 | <10 | <10 |
| Germall III | 980 | SA | 2,700 | <10 | <10 | <10 | <10 |
| IPBC | 20 | EC | <10 | <10 | <10 | <10 | <10 |
| | | PSA | <10 | <10 | <10 | <10 | <10 |
| | | BC | <10 | <10 | <10 | <10 | <10 |
| | | CAN | <10 | <10 | <10 | <10 | <10 |
| | | AN | <10 | <10 | <10 | <10 | <10 |
| Unpreserved | 0 | SA | >1E6 | 54,000 | 4,400 | 20 | >1E4 |
| | | EC | 80,000 | 67,000 | >1E4 | >1E4 | >1E4 |
| | | PSA | 2,000 | 4200 | >1E4 | >1E4 | >1E4 |
| | | BC | >1E6 | >1E6 | >1E4 | >1E4 | >1E4 |
| | | CAN | 990,000 | 320,000 | >1E4 | >1E4 | >1E4 |
| | | AN | 380,000 | 170,000 | >1E4 | >1E4 | >1E4 |

TABLE 9

COMPARISON OF ACTIVITY OF LIQUID GERMALL PLUS
AND GERMALL III/0.5% OR 0.8% IPBC
(SCREENING EMULSION)

| Preservative | Conc. | Organism | 48 hrs | 7 days | 14 days | 21 days | 28 days |
|---|---|---|---|---|---|---|---|
| LiqGermPlus | | SA | 110,000 | <10 | <10 | <10 | <10 |
| Germall II | 195 | EC | 2,600 | <10 | <10 | <10 | <10 |
| IPBC | 2.5 | PSA | <10 | <10 | <10 | <10 | <10 |
| | | BC | <10 | <10 | <10 | <10 | <10 |
| | | CAN | 240,000 | 120 | <10 | <10 | >1E4 |
| | | AN | 230 | <10 | <10 | <10 | <10 |
| LiqGermPlus | | SA | 2,800 | <10 | <10 | <10 | <10 |
| Germall II | 390 | EC | 1100 | <10 | <10 | <10 | <10 |
| IPBC | 5 | PSA | <10 | <10 | <10 | <10 | <10 |
| | | BC | <10 | <10 | <10 | <10 | <10 |
| | | CAN | 11,000 | <10 | <10 | <10 | 20 |
| | | AN | <10 | <10 | <10 | <10 | 100 |
| Germall III | 195 | SA | 260,000 | <10 | <10 | <10 | <10 |
| IPBC | 2.5 | EC | 4,300 | <10 | <10 | <10 | <10 |
| Liquid | | PSA | <10 | <10 | <10 | <10 | <10 |
| | | BC | <10 | <10 | <10 | <10 | <10 |
| | | CAN | 150,000 | <10 | <10 | <10 | >1E4 |
| | | AN | 200 | <10 | <10 | <10 | <10 |
| Germall III | 390 | SA | 170,000 | <10 | <10 | <10 | <10 |
| IPBC | 5 | EC | 2,500 | <10 | <10 | <10 | <10 |
| Liquid | | PSA | <10 | <10 | <10 | <10 | <10 |
| | | BC | <10 | <10 | <10 | <10 | <10 |
| | | CAN | 50,000 | <10 | <10 | <10 | >1E4 |
| | | AN | <10 | <10 | <10 | <10 | <10 |
| Germall III | 195 | SA | 70,000 | <10 | <10 | <10 | <10 |
| IPBC | 4 | EC | 1400 | <10 | <10 | <10 | <10 |
| Liquid | | PSA | <10 | <10 | <10 | <10 | <10 |
| | | BC | <10 | <10 | <10 | <10 | <10 |
| | | CAN | 41,000 | <10 | <10 | <10 | 40 |
| | | AN | <10 | <10 | <10 | <10 | <10 |
| Germall III | 390 | SA | 76,000 | <10 | <10 | <10 | <10 |
| IPBC | 8 | EC | 3,400 | <10 | <10 | <10 | <10 |
| Liquid | | PSA | <10 | <10 | <10 | <10 | <10 |
| | | BC | <10 | <10 | <10 | <10 | <10 |
| | | CAN | 14,000 | <10 | <10 | <10 | <10 |
| | | AN | <10 | <10 | <10 | <10 | <10 |

TABLE 9-continued

COMPARISON OF ACTIVITY OF LIQUID GERMALL PLUS
AND GERMALL III/0.5% OR 0.8% IPBC
(SCREENING EMULSION)

| Preservative | Conc. | Organism | 48 hrs | 7 days | 14 days | 21 days | 28 days |
|---|---|---|---|---|---|---|---|
| Unpreserved | 0 | SA | >1E6 | 54,000 | 4,400 | 20 | >1E4 |
| | | EC | 80,000 | 67,000 | >1E4 | >1E4 | >1E4 |
| | | PSA | 2,000 | 4200 | >1E4 | >1E4 | >1E4 |
| | | BC | >1E6 | >1E6 | >1E4 | >1E4 | >1E4 |
| | | CAN | 990,000 | 320,000 | >1E4 | >1E4 | >1E4 |
| | | AN | 380,000 | 170,000 | >1E4 | >1E4 | >1E4 |

TABLE 10

COMPARISON OF ACTIVITY OF GERMABEN II AND GERMABEN III
(SCREENING EMULSION)

| Preservative | Use Level | Organism | 48 hrs | 7 days | 14 days | 21 days | 28 days |
|---|---|---|---|---|---|---|---|
| Germaben II | 0.30% | SA | 480 | <10 | <10 | <10 | <10 |
| | | EC | <10 | <10 | <10 | <10 | <10 |
| | | PSA | <10 | <10 | <10 | <10 | <10 |
| | | BC | <10 | <10 | <10 | <10 | <10 |
| | | CAN | 20,000 | 100 | 2,600 | 380,000 | 380,000 |
| | | AN | <10 | <10 | <10 | <10 | <10 |
| Germaben II | 0.75% | SA | <10 | <10 | <10 | <10 | <10 |
| | | EC | <10 | <10 | <10 | <10 | <10 |
| | | PSA | <10 | <10 | <10 | <10 | <10 |
| | | BC | <10 | <10 | <10 | <10 | <10 |
| | | CAN | <10 | <10 | <10 | <10 | <10 |
| | | AN | <10 | <10 | <10 | <10 | 100 |
| Germaben III | 0.30% | SA | 7,000 | <10 | <10 | <10 | <10 |
| | | EC | <10 | <10 | <10 | <10 | <10 |
| | | PSA | <10 | <10 | <10 | <10 | <10 |
| | | BC | <10 | <10 | <10 | <10 | <10 |
| | | CAN | 14,000 | 120 | >1E4 | 470,000 | 190,000 |
| | | AN | <10 | <10 | <10 | <10 | <10 |
| Germaben III | 0.75% | SA | <10 | <10 | <10 | <10 | <10 |
| | 5 | EC | <10 | <10 | <10 | <10 | <10 |
| | | PSA | <10 | <10 | <10 | <10 | <10 |
| | | BC | <10 | <10 | <10 | <10 | <10 |
| | | CAN | <10 | <10 | <10 | <10 | <10 |
| | | AN | <10 | <10 | <10 | <10 | <10 |
| Unpreserved | 0 | SA | >1E6 | 46,000 | >1E4 | 60 | >1E4 |
| | | EC | >1E6 | 170,000 | >1E4 | >1E4 | >1E4 |
| | | PSA | 690 | 24000 | >1E4 | >1E4 | >1E4 |
| | | BC | >1E6 | >1E6 | >1E4 | >1E4 | >1E4 |
| | | CAN | 440,000 | >1E4 | >1E4 | >1E4 | >1E4 |
| | | AN | 87,000 | >1E4 | >1E4 | >1E4 | >1E4 |

TABLE 11

COMPARISON OF ACTIVITY OF GERMABEN IIE AND GERMABEN IIIE
(SCREENING EMULSION)

| Preservative | Use Level | Organism | 48 hrs | 7 days | 14 days | 21 days | 28 days |
|---|---|---|---|---|---|---|---|
| Germaben IIE | 0.30% | SA | 580 | <10 | <10 | <10 | <10 |
| | | EC | <10 | <10 | <10 | <10 | <10 |
| | | PSA | <10 | <10 | <10 | <10 | <10 |
| | | BC | <10 | <10 | <10 | <10 | <10 |
| | | CAN | 1,600 | <10 | <10 | <10 | <10 |
| | | AN | <10 | <10 | <10 | <10 | <10 |
| Germaben IIE | 0.75% | SA | <10 | <10 | <10 | <10 | <10 |
| | | EC | <10 | <10 | <10 | <10 | <10 |
| | | PSA | <10 | <10 | <10 | <10 | <10 |
| | | BC | <10 | <10 | <10 | <10 | <10 |
| | | CAN | <10 | <10 | <10 | <10 | <10 |
| | | AN | <10 | <10 | <10 | <10 | <10 |

TABLE 11-continued

COMPARISON OF ACTIVITY OF GERMABEN IIE AND GERMABEN IIIE (SCREENING EMULSION)

| Preservative | Use Level | Organism | 48 hrs | 7 days | 14 days | 21 days | 28 days |
|---|---|---|---|---|---|---|---|
| Germaben IIIE | 0.30% | SA | 270 | <10 | <10 | <10 | <10 |
| | | EC | <10 | <10 | <10 | <10 | <10 |
| | | PSA | <10 | <10 | <10 | <10 | <10 |
| | | BC | <10 | <10 | <10 | <10 | <10 |
| | | CAN | 4,000 | <10 | <10 | <10 | 90 |
| | | AN | <10 | <10 | <10 | <10 | <10 |
| Germaben IIIE | 0.75% | SA | <10 | <10 | <10 | <10 | <10 |
| | | EC | <10 | <10 | <10 | <10 | <10 |
| | | PSA | <10 | <10 | <10 | <10 | <10 |
| | | BC | <10 | <10 | <10 | <10 | <10 |
| | | CAN | <10 | <10 | <10 | <10 | <10 |
| | | AN | <10 | <10 | <10 | <10 | <10 |

Discussion of Challenge Testing Results

The 28 day challenge results reported in Tables 3–11 above demonstrate the effectiveness of the preservative composition of the invention in a use emulsion composition against a wide range of bacteria and fungi organisms.

While the invention has been described with particular reference to certain embodiments thereof, it will be understood that changes and modifications may be made which are within the skill of the art. Accordingly, it is intended to be bound only by the following claims, in which:

What is claimed is:

1. A reaction product of allantoin and formaldehyde which has the formula

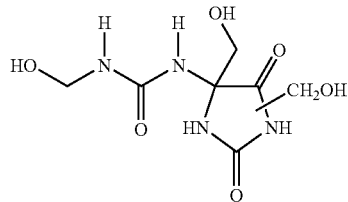

which is

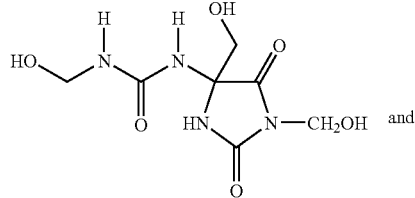

-continued

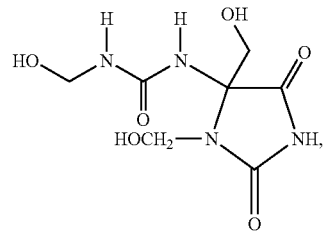

or mixtures thereof, made in a mole ratio of 1:2.75–3.25, respectively, having a level of free formaldehyde of <0.1%, and methylene diol of about 580–1385 ppm, which provides long-lasting anti-microbial activity, particularly against the organism *B. cepacia*, at a use level of 0.05–0.5% by weight of the reaction product.

2. A reaction product according to claim 1 having a pH of about 7.2.

3. A reaction product according to claim 1 which is made under controlled reaction conditions of a pH of 5.0–70 and 40–85° C.

4. A reaction product according to claim 1 wherein said mole ratio is 1:3.

5. A solution of the reaction product of claim 1 at a use level of 0.05–0.5% by weight in a solvent.

* * * * *